United States Patent
Adams et al.

(10) Patent No.: US 8,609,067 B2
(45) Date of Patent: Dec. 17, 2013

(54) METHOD OF MEASURING PROPULSION IN LYMPHATIC STRUCTURES

(75) Inventors: Kristen Adams, Houston, TX (US); Ruchi Sharma, Houston, TX (US); John C. Rasmussen, Spring, TX (US); Eva M. Sevick-Muraca, Montgomery, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/189,333

(22) Filed: Jul. 22, 2011

(65) Prior Publication Data
US 2011/0280811 A1 Nov. 17, 2011

Related U.S. Application Data

(63) Continuation of application No. 11/844,864, filed on Aug. 24, 2007, now abandoned.

(60) Provisional application No. 60/840,256, filed on Aug. 25, 2006, provisional application No. 60/823,481, filed on Aug. 24, 2006.

(51) Int. Cl.
*A61K 49/00* (2006.01)

(52) U.S. Cl.
USPC .............................................. 424/9.6; 424/9.1

(58) Field of Classification Search
None
See application file for complete search history.

(56) References Cited

U.S. PATENT DOCUMENTS 7,181,266 B2 * 2/2007 Frangioni et al. ............. 600/476
2008/0240535 A1 * 10/2008 Frangioni et al. ............. 382/131

OTHER PUBLICATIONS

Uren et al ("Patterns of Lymphatic Drainage from the Skin in Patients with Melanoma," J Nud Med 2003; 44:570-582).*

* cited by examiner

*Primary Examiner* — Suzanne Ziska
(74) *Attorney, Agent, or Firm* — Conley Rose, P.C.

(57) ABSTRACT

Novel methods and imaging agents for functional imaging of lymph structures are disclosed herein. Embodiments of the methods utilize highly sensitive optical imaging and fluorescent spectroscopy techniques to track or monitor packets of organic dye flowing in one or more lymphatic structures. The packets of organic dye may be tracked to provide quantitative information regarding lymph propulsion and function. In particular, lymph flow velocity and pulse frequency may be determined using the disclosed methods.

17 Claims, 16 Drawing Sheets

METHOD OF MEASURING PROPULSION IN LYMPHATIC STRUCTURES

CROSS-REFERENCE TO RELATED APPLICATIONS

The present application claims the benefit of U.S. Provisional Application Ser. No. 60/840,256, filed Aug. 25, 2006, and U.S. Provisional Application Ser. No. 60/823,481, filed Aug. 24, 2006, each of which is herein incorporated by reference in their entireties for all purposes. U.S. application Ser. No. 11/844,807 entitled Imaging Agents for Functional Imaging of Lymphatic Structures, filed Aug. 24, 2007, is herein incorporated by reference in its entirety for all purposes.

STATEMENT REGARDING FEDERALLY SPONSORED RESEARCH OR DEVELOPMENT

This work was supported by the National Institutes of Health (R01 CA112679).

BACKGROUND

1. Field of the Invention

This invention relates generally to the field of biomedical imaging. More specifically, the invention relates to a method of functionally imaging and measuring lymphatic function by assessing lymph propulsion in lymphatic structures.

2. Background of the Invention

The lymphatic system is made of vessels or ducts that begin in tissues and are designed to carry lymph fluid to local lymph nodes where the fluid is filtered and processed and sent to the next lymph node down the line until the fluid reaches the thoracic duct where it enters the blood stream. Lymph vessels infiltrate all tissues and organs of the body. Lymph fluid is generated from capillaries which, because of tissue motion and hydrostatic pressure, enters the lymph vessels carrying with it local and foreign substances and materials from the tissues. These local and foreign molecular, micromolecular, and macromolecular substances include antigens, infectious agents, particles and cells. Lymph nodes, the lymph "filters," consist of essentially two major compartments: the fluid spaces (or sinuses) and the cellular elements. There is one major sinus at the outer margin of the node that feeds a maze of sinuses that serve to percolate the fluid slowly towards the hilum of the node from where it is carried downstream. The sinuses are lined by macrophages that phagocytose materials carried by the fluid, particularly if the materials have certain surface charges or specific shapes. The remainder of the cellular elements in the lymph node performs the immunologic function of the node. In this regard, the lymph nodes process fluid by sieving and phagocytosis to remove particulate and cell materials delivered by the lymphatic vessels, thereby cleaning it before it is returned to the blood stream.

The impairment of lymphatic transport capacity occurs due to either 1) lymph vessel damage and subsequent insufficient repair processes, or 2) congenital defects leading to abnormal lymph vessel development. Regardless of the cause, the impairment causes fluid and protein accumulation, which in turn leads to lymphedema. Lymphedema is a lifelong condition progressing from swelling and scarring to immune dysregulation and malnutrition. No curative treatment exists for lymphedema, which afflicts 300 million people worldwide. Congenital or primary lymphedema afflicts 1 in every 6,000 newborns and can also appear at the onset of puberty. Acquired or secondary lymphedema is caused by the filaria parasite (in a condition referred to as elephantiasis) or by trauma due to radiation therapy, infiltrating cancer, surgery, or infection. In developing-world countries, 100 million people are afflicted worldwide by filariasis. In Western countries, acquired lymphedema afflicts 3 to 5 million people. The etiology for trauma-associated, acquired lymphedema is thought to arise from the interruption of lymph channels coupled with postsurgical infection or radiation-induced skin reaction. The onset of symptoms, however, can occur from days, weeks, to years following the initial trauma, striking at a rate cited between 6 and 62.5% of breast cancer survivors who have undergone axillary lymph node dissection, up to 64% of all patients who undergo groin dissections, and 25% of all radical hysterectomy patients. Little is known about the molecular or functional basis of acquired lymphedema or which persons could be at risk for the condition. There is a paucity of strategies for predicting or managing lymphedema due in part to the lack of diagnostic imaging approaches to noninvasively and routinely measure lymphatic function. Since lymph function is also implicated in diseases of significant prevalence (e.g. diabetes, obesity, cancer, and asthma), the ability to quantitatively image lymph function could have substantial impact on the health of the world's population.

The ability to functionally image the lymphatic system non-invasively may be clinically relevant for the prevention, diagnosis, treatment, and research of lymphatic diseases. However, there are presently very few technologies with the ability to non-invasively image the lymphatic system in vivo and in real time.

Consequently, there is a need for a non-invasive imaging methods and imaging agents for dynamically assessing lymph function in vivo.

BRIEF SUMMARY

Novel methods and imaging agents for functional imaging of lymph structures are disclosed herein. Embodiments of the methods utilize highly sensitive optical imaging and fluorescent spectroscopy techniques to track or monitor packets of organic, soluble dyes being propelled through one or more lymphatic structures. The packets of organic dye may be tracked to provide quantitative information regarding lymph propulsion and function. Thus, the disclosed methods provide non-invasive ways of assessing lymph function in deep lymph structures. The organic dyes may be excited at the near-infrared wavelength regime of 750-800 nm with fluorescence >800 nm allowing for deep tissue imaging of lymphatic function.

In addition, novel imaging agents targeted to lymph endothelial cell receptors are disclosed. The disclosed imaging agents incorporate biological molecules such as hyaluronic acid which bind to lymph endothelial cell receptors. Lymph endothelial cell receptor expression may be related to the beginnings of tumor formation. As such, embodiments of the imaging agents may be used to stain lymph structures for detailed imaging of lymph architecture as well as serving as potential markers for tumor angiogenesis, tumor metastases, etc. Further advantages and features of the methods and imaging agents are described in more detail below.

In an embodiment, a method of measuring lymph propulsion comprises administering an organic, soluble dye to one or more lymph structures. The organic dye generally has an excitation wavelength. The method further comprises illuminating the tissue surface with excitation light to excite the organic dye. In addition, the method comprises detecting the emission from the organic dye. The method comprises capturing a plurality of images of the one or more lymph structures for a period ranging from about 1 minute to about 30 minutes. The method also comprises tracking one or more packets of organic dye flowing through the lymph structure from the plurality of images of the one or more lymph structures to quantitatively measure lymph propulsion. The method may be performed non-invasively in intact living subjects.

In another embodiment, a method of determining pulse frequency in one or more lymph structures comprises administering an organic dye to the one or more lymph structures under a tissue surface. The method additionally comprises illuminating the tissue surface with excitation light to excite the organic dye. Moreover, the method comprises determining a target region of the one or more lymph structures. Furthermore, the method comprises continuously measuring fluorescent intensity from the organic dye at the target region for a time period of at least about 1 minute. The method also comprises determining a number of fluorescent intensity peaks over the time period, the intensity peaks representing one or more packets of organic dye being propelled through the one or more lymphatic structures, and dividing the number of intensity peaks by the time period to determine the pulse frequency of the one or more lymph structures.

In an embodiment, a method of determining lymph flow velocity in one or more lymph structures comprises administering an organic dye to the one or more lymph structures under a tissue surface. Additionally, the method comprises illuminating the tissue surface with excitation light to excite the organic dye. The method further comprises determining at least a first and a second target region along the one or more lymph structures having a distance between the first and second target regions. Moreover, the method comprises measuring a time period for a packet of organic dye to pass through the target regions. The method also comprises dividing the distance by the time period to determine the lymph flow velocity in the one or more lymph structures.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which:

FIG. 10A shows ROI selected on leg lymph vessel stained with HA-NIR dye. FIG. 10B shows ROI selected on leg lymph vessel with trafficking ICG. FIG. 10C shows a comparison of intensity profile as a function of time for selected ROI;

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection, or through an indirect electrical connection via other devices and connections.

As used herein, the term "lymphatic structure(s)" refers to all or a portion of structures that make up a mammalian lymphatic system including without limitation, lymph nodes, collecting vessels, lymph trunks, lymph ducts, capillaries, or combinations thereof.

As used herein, the term "near-infrared" refers to electromagnetic radiation at wavelengths ranging from about 750 nm to about 900 nm.

DETAILED DESCRIPTION OF THE PREFERRED EMBODIMENTS

Figure 1:
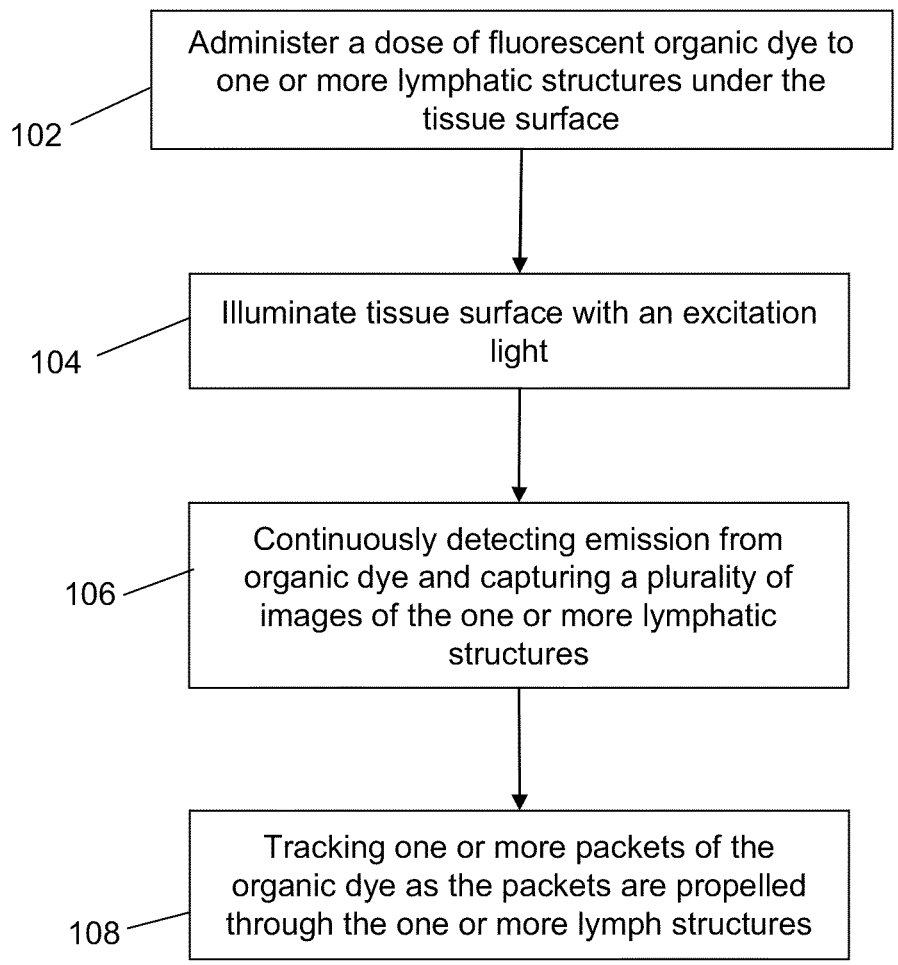
FIG. 1 is a flow diagram of an embodiment of a method of measuring lymph propulsion.

FIG. 1 illustrates a flow diagram of a method 100 of measuring propulsion in one or more lymphatic structures. As used herein, the term "propulsion" and other tenses and forms thereof refers to the act of pumping or driving forward a fluid. In 102, a dose or bolus of fluorescent organic dye may be administered to one or more lymph structures under the tissue surface of a patient. The organic dye generally has an excitation wavelength at which it will fluoresce or emit light at an emission wavelength. An excitation light encompassing the excitation wavelength may then be illuminated on the target tissue surface to excite the organic dye in 104. Upon illumination, emissions from the organic dye may be continuously sensed or detected at the excitation wavelength in 106 to capture fluorescent images of the one or more lymphatic structures. Packets or masses of organic dye may be tracked, observed or imaged being propelled through the lymph structures in 108. The images that have been continuously acquired or captured are used to create a sequence of images (i.e. a movie) to track the packets of organic dye for quantitative assessment and measurement of lymph propulsion.

Figure 2:
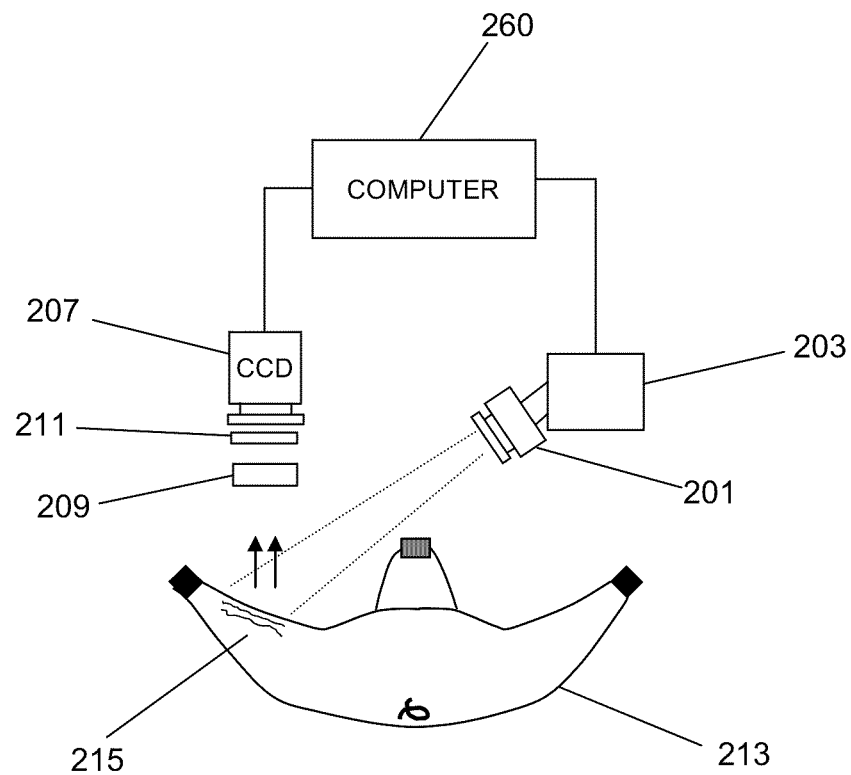
FIG. 2 illustrates a schematic of a system that may be used in conjunction with embodiments of the method.

FIG. 2 illustrates an example of a system 200 that may be used to implement embodiments of the disclosed method including an excitation light source 201. Briefly, an excitation light source 201 may be mounted on a stepper motor 203 to enable scanning across the tissue surface 213 (i.e. patient) at the desired target tissue region 215. The excitation light may be shaped using a lens 205. Images may be acquired by an intensified CCD camera 207. An image intensifier 209 and filter 211 may be placed in front of the lens of CCD camera 207. Filter 211 may comprise any suitable filter to pass only the emitted light at the excitation wavelength from the organic dye. The captured images may be processed and stored in computer 260. Further examples of and variations on such a system may be found in U.S. Pat. Nos. 5,865,754 and 7,054,002, incorporated herein by reference in their entireties for all purposes.

In embodiments, the imaging agent used in conjunction with the disclosed methods is preferably an organic dye. As used herein, the term "organic dye" refers to all non-particulate, compounds that do not contain mineral or inorganic components and are capable of fluorescence. Preferably, the organic dye is soluble in liquid solvents such as water. Examples of suitable organic dyes include without limitation, tricarbocyanine dyes, bis(carbocyanine) dyes, dicarbocyanine dyes, indol-containing dyes, polymethine dyes, acridines, anthraquinones, benzimidazole, indolenines, napthalimides, oxazines, oxonols, polyenes, porphins, squaraines, styryls, thiazols, xanthins, or combinations thereof. In a specific embodiment, the organic dye is indocyanine green. The organic dyes may have excitation wavelengths ranging from about 700 nm to about 1000 nm, preferably from about 750 nm to about 900 nm, more preferably from about 780 nm to about 800 nm. In particular, the organic dyes may have excitation wavelengths in the near-infrared range (NIR).

The organic dye is typically diluted in a liquid solution such as saline solution. The concentration of organic dye in solution may range from about 1 μM to about 400 μM, preferably from about 10 μM to about 200 μM, more preferably from about 25 μM to about 100 μM. In addition, any appropriate amount of the organic dye may be administered to the lymph structure(s). In some embodiments, the amount of organic dye administered may range from <1 μg to 10 mg, preferably from about <1 μg to about 1 mg, more preferably from about <1 μg to about 100 μg.

Referring back to FIG. 1, the organic dye may be administered to the lymphatic system through any suitable means 102. For example, the organic dye may be delivered using a syringe. In particular, the organic dye may be administered intradermally or into the skin. Without being limited by theory, the lymphatic plexus may pick up packets or masses of the organic dye and transit the packets of organic dye through lymph vessels to the lymph nodes. Alternatively, the organic dye is administered using a catheter system inserted directly into the lymphatic system. Because of the high sensitivity of the disclosed methods, lymphatic structures deep beneath the tissue surface may be imaged. In particular, the lymph structures may be located at a depth of at least about 1 cm below the tissue surface, preferably at least about 2 cm, more preferably at least about 3 cm below the tissue surface.

To excite the organic dye in the lymphatic system, an excitation light may be illuminated on the tissue surface over the targeted lymph nodes and/or channels in 104 by an excitation light source 201 as shown in FIG. 2. Excitation light source 201 may be any light source known to those of skill in the art. Examples of suitable light sources include without limitation laser diodes, semiconductor laser diodes, gas lasers, light emitting diodes (LEDs), or combinations thereof. In an embodiment, excitation light source may comprise a Gaussian light source. As defined herein, a Gaussian light source is a light source in which the spatial distribution of the emitted light is a Gaussian distribution.

Preferably, the excitation light source 201 is a continuous wave light source which emits a continuous wave light. The light source may emit light having wavelengths ranging from about 700 nm to about 800 nm, preferably from about 725 nm to about 775 nm, more preferably from about 745 nm to about 755 nm. Alternatively, the excitation light source 201 may be a time varying light source. Thus, the intensity of the excitation light source 201 may vary with time. In other words, the excitation light source may emit an intensity-modulated light beam. The intensity modulation of excitation light source may comprise without limitation, sinusoidal, square wave, or ramp wave modulation. In addition, the excitation light source 201 may also be pulsed at certain frequencies and repetition rates. The frequency and repetition rates may also be varied with time. The time variation of the excitation light source may be about 1 to about 3 orders of magnitude of the lifetime of the organic dyes used in conjunction with embodiments of the method.

Upon illumination of the tissue surface by the excitation light, the organic dye administered to the lymphatic system emits fluorescent light. A sensor may be used to detect or sense the emissions from the fluorescent organic dye. The sensor is preferably capable of detecting fluorescent light emitted from the fluorescent targets and detecting excitation light reflected from the medium. In an embodiment, the sensors may comprise an intensified charge-coupled camera. Other examples of suitable sensors include without limitation, gated or non-gated electron multiplying (EM)-CCD or intensified (ICCD) cameras. The sensor may further comprise any suitable filters or polarizers necessary to measure the appropriate wavelengths of light required for fluorescent optical tomography and imaging.

In an embodiment, fluorescent emissions from the organic dye may be continuously detected in 106. The emissions may be continuously detected by continuously capturing or acquiring images of the emitted light from the organic dye to create a sequence of real-time images (i.e. a movie or video) of lymph propulsion through the lymph structures. The image may be captured for a time period ranging from about 100 milliseconds to about 30 minutes, preferably from about 1 minute to about 20 minutes, more preferably from about 5 minutes to about 15 minutes. Moreover, the images may be captured or recorded at any suitable integration time ranging from about 1 millisecond to about 5 seconds, preferably from about 10 milliseconds to about 1 second, and more preferably from about 100 milliseconds to about 800 milliseconds. Accordingly, depending on the time period and the frame rate, the images collected may range anywhere from 100 images to over 1,000 images.

An aspect of embodiments of the disclosed method is the ability to track or monitor, in real-time, packets of organic dye being propelled or trafficked through the one or more target lymph structures. It is believed that the packets of organic dye represent real-time physiological propulsion of fluids through the lymph structures which has previously never been seen before using any imaging technique. By tracking packets of organic dye as they are pumped through the lymph structures, lymph propulsion and function may be quantitatively and accurately measured. In addition, the sequence of recorded images provides a permanent optical recording of one or more packets or masses of organic dye being propelled or trafficked through the lymph structure upon which further analysis may be performed to assess lymph functionality.

Figure 3:
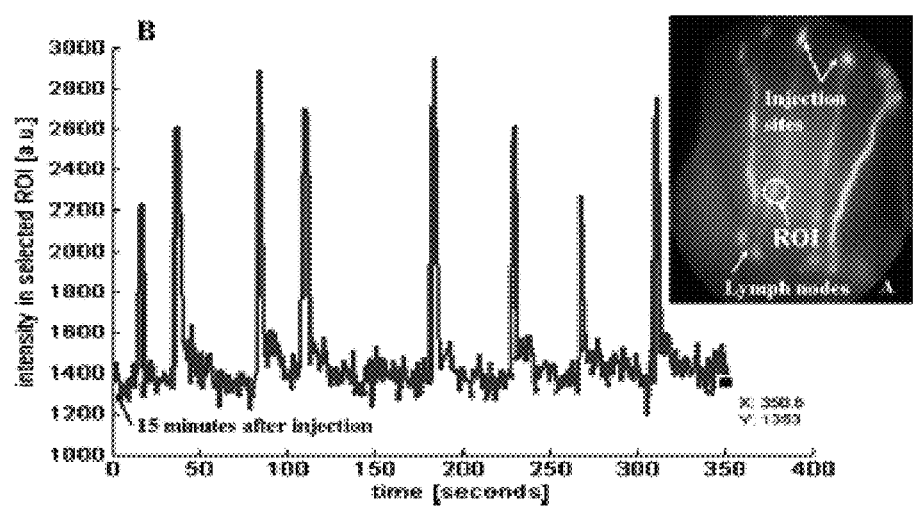
FIG. 3 is a plot of intensity versus time of the target region of interest (ROI) illustrating the pulsatile motion of functioning lymph vessels after organic dye was intradermally administered.

To quantify pulsatile lymph flow, a stationary target area or region may be identified on a fluorescent lymph vessel as shown in FIG. 3A. The target area or region is a point along the lymph structure at which measurements may specifically be taken. The fluorescent intensity at the specified target area may then be measured continuously over a given period of time. As a packet of organic dye passes through the lymph structure, a corresponding spike or peak in fluorescent intensity may be measured. A plot of intensity over time as shown in FIG. 3B provides a good illustration of the measurement. The pulse frequency of the lymph structure may then be quantified by dividing the number of pulse measured by the measurement time period. For example, if eight intensity peaks were measured over a time period of 5 minutes, the pulse frequency would equal about 1.6 pulses/min.

In another embodiment, the functional status of lymph channels may be characterized by measuring the velocity of the transiting organic dye "packets." A plurality of target regions may be assigned along the length of the target lymph structure. Furthermore, the plurality of target regions may comprise any distribution along the lymph structure. For example, a target region may be assigned every 2 mm along a lymph structure.

Figure 4A:
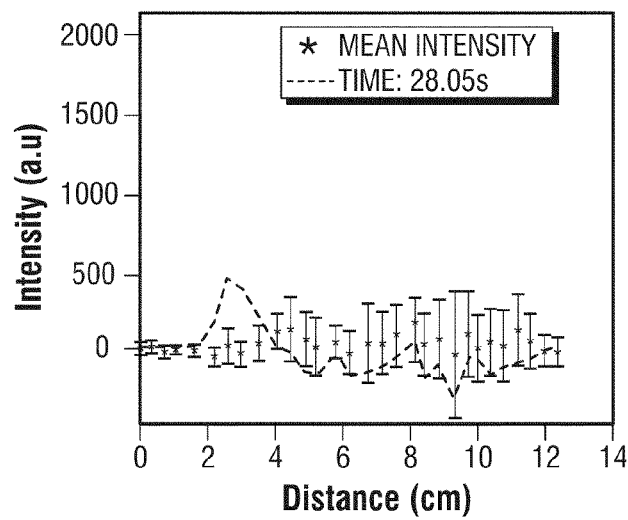
FIG. 4a-c are plots of average intensity in ROI's at increasing distance along a lymph vessel away from the administration site away at 28, 30, and 35 seconds from time of injection respectively.
Figure 4B:
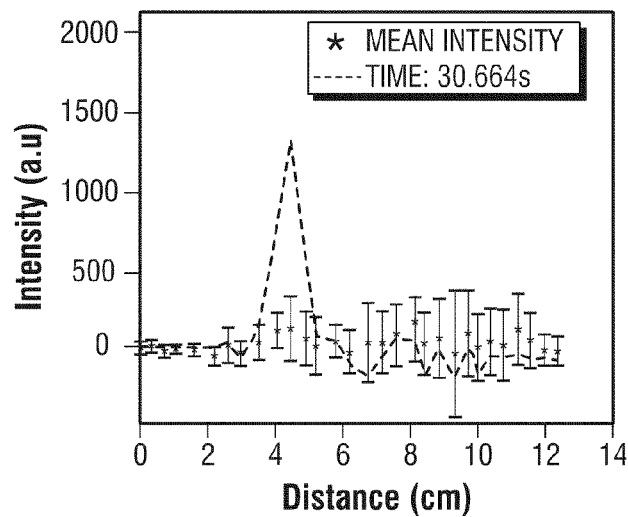
Figure 4C:
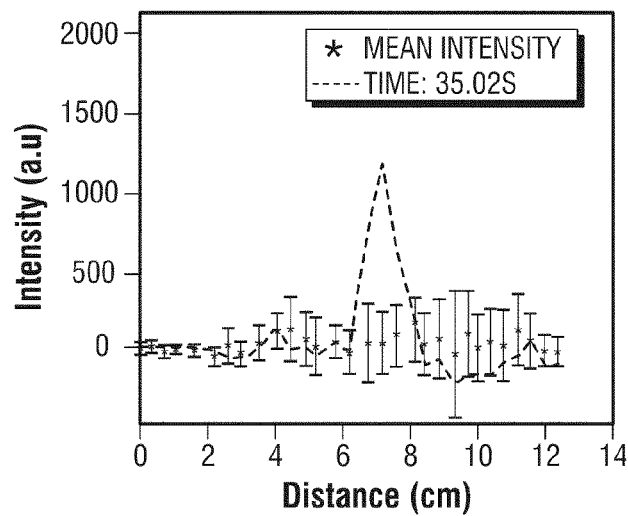

As a further illustration, FIG. 4 shows a plot of "snapshots" of different target regions of fluorescent intensity as a function of vessel length from the site of administration at approximately 28, 30, and 35 seconds. Superimposed on each plot are the time-averaged target region fluorescent intensities with standard deviations plotted as a function of vessel length. As depicted in the image frames, a packet of organic dye, as indicated by the dashed curve, may be clearly differentiated from the time averaged baseline fluorescent intensity, illustrated by the asterisks with error bars.

To determine the velocity of propelled packet, a first and second target region on the lymph structure may be defined. The target regions may be any distance apart on the lymph structure. In some embodiment, the target region may be the entry of the lymph structure and the second target region may be the exit of the lymph structure such that the distance is the entire length of the lymph structure. Once the target regions have been defined, the peak of the fluorescent intensity representing a packet of organic dye may be tracked along the known vessel distance. A time period is determined as a packet is propelled through a first target region at time "t" and then propelled through the second target region at time "t+x," where x is a known elapsed time. The velocity may then be calculated as the distance between the target regions divided by the elapsed time between the packet passing through the first and second target regions. The resulting lymph velocity may be calculated using any suitable units (e.g. m/s, in/s, etc). Thus, the above disclosed methods provide a quantitative, simple, and non-invasive way to assess lymph functionality using pulse frequency and/or lymph flow velocity.

In further embodiments, it is envisioned that the disclosed methods may be used in conjunction with tomographic imaging to produce three dimensional images of lymph propulsion. Tomographic techniques with patterned illumination as disclosed in U.S. patent application Ser. No. 11/688,732, incorporated herein by reference in its entirety for all purposes, may be used to acquire deep tissue images of lymph propulsion.

Figure 5:
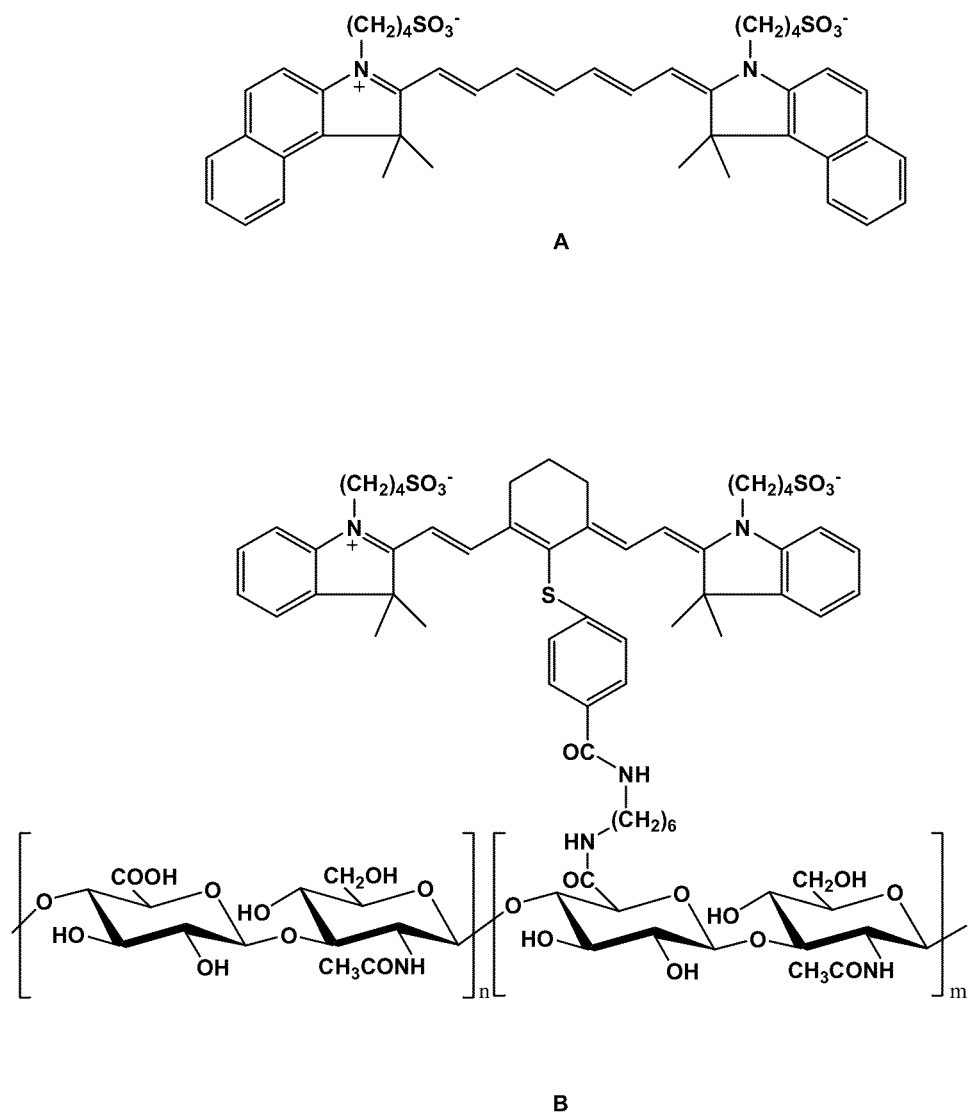
FIG. 5A shows the structure of an exemplary organic dye, indocyanine green.
FIG. 5B shows an embodiment of a modified imaging agent comprising a fluorescent dye conjugated to a polysaccharide such as hyaluronic acid.

FIG. 5 illustrates an embodiment of an imaging agent that may be used to stain one or more lymph structures for the quantitative assessment of lymph function. In an embodiment, the imaging agent comprises an organic dye coupled to one or more binding moieties. The one or more binding moieties may provide the ability to bind the organic dye to lymph structures and provide detail of the lymph architecture, detect lymph nodes, and assess tumor lymphangiogenesis.

The organic dye may be any of the organic dyes described previously above. In particular, the organic dye is a compound that exhibits fluorescence at near-infrared wavelengths when exposed to excitation light. Examples of the organic dye which may be used in conjunction with the one or more binding moieties include without limitation, indol-containing dyes, carbocyanine-containing dyes, polymethine dyes, acridines, anthraquinones, benzimidazole, indolenines, napthalimides, oxazines, oxonols, polyenes, porphins, squaraines, styryls, thiazols, xanthins, other NIR dyes known to those of skill in the art, or combinations thereof. In an embodiment, the organic dye is IR-783 as shown in FIG. 5. Furthermore, the organic dye preferably has an excitation wavelength in the near-infrared range. In particular, the organic dye may have excitation wavelengths ranging from about 700 nm to about 1000 nm, preferably from about 720 nm to about 900 nm, more preferably from about 750 nm to about 850 nm.

The binding moiety may comprise any molecule or compound which preferentially binds to lymph endothelial cells. Examples of suitable targeting moieties include without limitation, amino acids, receptors, enzymes, signaling molecules, peptides, proteins, oligopeptides, or combinations thereof. Furthermore, binding moiety may comprise biological molecules such as without limitation, proteoclycans, glycosaminoglycans (GAGs), carbohydrates, polysaccharides, or combinations thereof. In an embodiment, targeting moiety comprises hyaluronic acid or hyaluranon (HA) as shown in FIG. 5. HA is a high molecular weight polysaccharide found in extracellular matrix of all types of tissues. It is a linear polymer of (1-β-4) D-glucoronic acid (1-β-3) N-acetyl-D-glucosamine. The HA coupled to the organic dye may have a molecular weight ranging from about 1,000 Da to about 25,000 Da. The subscripts "m" and "n" in FIG. 5 denote integers representing the number of repeating units. The ratio of "m" and "n" preferably may range from 1:1 to 2:100. In addition, "m" and "n" may comprise integers ranging from 1,000 to 25,000. HA facilitates mitosis, cell migration during wound healing and inflammation and embryonic morphogenesis. Turnover rate of the HA varies from 0.5 to a few days depending on the tissue type. HA is naturally transported through the lymph system to lymph nodes where 90% of the glucosaminoglycan is degraded and the remaining 10% is broken down in the liver. Consequently, the conjugated HA-dye is a particular imaging agent directed to lymph.

Generally, the binding moiety is capable of binding to a hyaluronic acid binding receptor or receptors which bind to HA. In a particular embodiment, the binding moiety is specific to a lymph vascular cell receptor such as without limitation, LYVE-1 receptor (Lymphatic Vessel Endothelial Receptor 1). LYVE-1 is a receptor that is a specific marker of lymph endothelium. Without being bound by theory, the LYVE-1 receptor on the lymphatic endothelium may sequester HA on the lymph vessel endothelium. Hence, HA conjugated to a near infra-red fluorescent organic dye may be used to stain one or more lymphatic structures. It is envisioned that an organic dye may be coupled to one or more binding moieties which preferentially bind to other lymph endothelial cell receptors besides LYVE-1. The binding moiety may also bind to hyaluranon cell receptors such as without limitation, hyaluranon receptor for endocytosis (HARE), which may be responsible for polysaccharide uptake in the lymph nodes.

Since the imaging agent is bound to the lymph structure, the structure is "stained" and the architecture of the lymph structure may be quantitatively imaged. Thus, an advantage of the disclosed imaging agents is their ability to remain in the lymph structure for long periods of time as opposed to other imaging agents which are quickly cleared from the lymphatic system after injection. Embodiments of the imaging agent are particularly useful in targeting the lymph node as it is known to degrade polysaccharides such as hyaluronic acid. The ability to image the architecture of lymphatics and specifically, the lymph nodes, is clinically relevant for the prevention, diagnosis, treatment, and research of lymphatic diseases and cancer, as well as for surgical planning.

Therefore, in another embodiment, the imaging agent modified with the one or more binding moieties may be used in a method of imaging one or more lymph structures. In particular, the imaging agent may be used to stain and image the lymph nodes. System 200 as shown in FIG. 2 may be used to image the stained lymph structures.

The modified imaging agent (e.g. IR-783 functionalized with HA) may be administered to one or more lymph structures under the tissue surface. The modified imaging agent may be administered either (i) intradermally into the interstitial space for transport into the lymphatics, (ii) directly into the lymphatics via cannulation of the lymphatic vessels, or (iii) intravenously, for transport across the vasculature into the lymph nodes.

The imaging agent may be diluted in a solution such as without limitation, saline solution. The concentration of the modified imaging agent in solution may range from about 1 µM to about 400 µM, preferably from about 10 µM to about 200 µM, more preferably from about 25 µM to about 100 µM. Furthermore, different amounts of the imaging agent may be administered or delivered to the one or more lymph structures. For example, the amounts administered may range from <1 µg to 10 mg, preferably from about <1 µg to about 1 mg, more preferably from about <1 µg to about 100 µg.

The modified imaging agent may bind to the endothelial lining of the one or more lymph structures and stain the structures. The tissue surface may then be illuminated with excitation light to excite the imaging agent at its excitation wavelength. Emissions from the imaging agent may be detected and captured as fluorescent images.

Moreover, in addition to staining the lymph structures, due to the preferential binding of the imaging agent to lymph endothelial cell receptors, embodiments of the imaging agent may be used to detect and/or measure the expression of such receptors.

Embodiments of the disclosed imaging agents may be used to sense hyaluronidase, an enzyme which degrades HA. Studies have shown that hyaluronidase may be a marker for cancer. Accordingly, the ability to optically detect an increase in hyaluronidase activity may be useful in early detection of metastases and/or tumor formation. Thus, a method of sensing hyaluronidase may comprise administering a concentration of a modified imaging agent (e.g. HA-modified organic dye). The modified imaging agent binds and stains the lymph structures. The initial fluorescent intensity may be measured and recorded. Over time, the fluorescent intensity may be monitored. An increased hyaluronidase may be sensed by a corresponding increase in the fluorescent intensity. Without being limited by theory, it is believed that the close spacing of the dye molecules may cause fluorescent quenching. The cleavage of the HA polysaccharide may result in a reduction in the quenching and an increase in fluorescent yield. Thus, an increase in fluorescence over time may signal the presence of hyaluronidase.

By altering the concentration of modified or conjugated imaging agent, the fluorescent intensity of the imaging agent may be tuned to sense hyaluronidase. Since hyaluronan degradation occurs primarily in the lymph nodes, this may be used to provide a selective method for imaging lymph nodes with this specificity and sensitivity.

Figure 6:
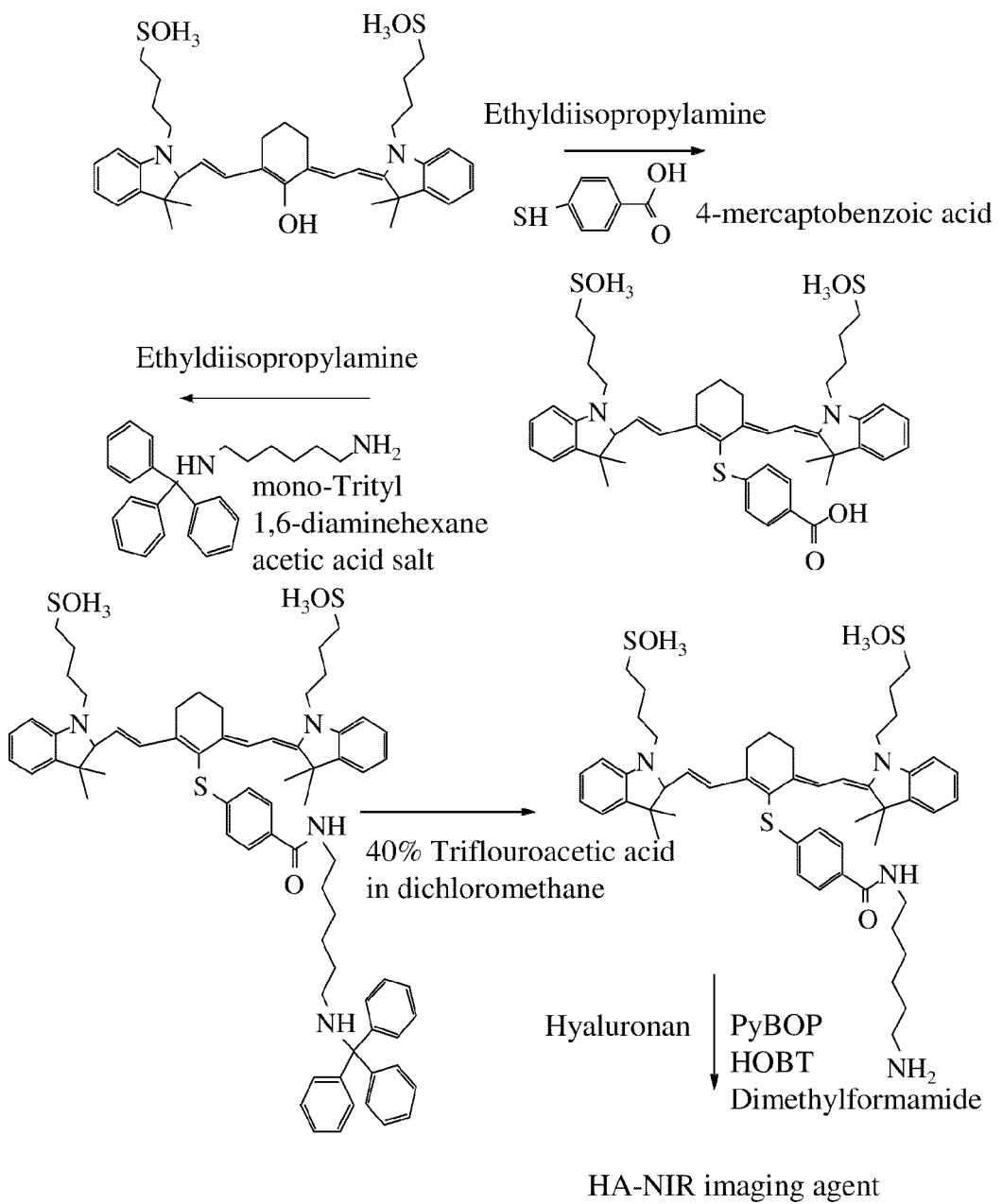
FIG. 6 shows a schematic of an embodiment of modifying an imaging agent.

Now referring to FIG. 6, in an embodiment, a method of making a lymph binding imaging agent comprises modifying or functionalizing an organic fluorescent dye such as IR-783 dye. In particular, an organic dye is functionalized to contain an amine group. Any method known to one of skill in the art may be used to aminate (i.e. attach an amine group) the organic dye. In a specific embodiment, the organic dye may be reacted with a mercapto or thiol compound such as mercaptobenzoic acid to form an intermediate linking group. Other mercapto compounds such as mercaptohexadecanoic acid may be used form an intermediate linking group. The intermediate linking group may be modified with a trityl amine-containing compound (e.g. mono-trityl 1,6-diaminohexan acetic acid salt) to form an alkyl diamine linkage group. The diamine linkage group may contain an alkyl chain having from 2 to 10 carbon atoms. In a specific embodiment, the linkage group is a hexane diamine linkage group. The binding moiety (e.g. hyaluronic acid) may then be coupled to the organic dye via the alkyl diamine group.

To further illustrate various illustrative embodiments of the invention, the following examples are provided.

EXAMPLE 1

Material and Methods

Animal Models

Four, two-month old, 60 lb white Yorkshire swine (K Bar Livestock, HC 69 Box 270 Sabinal, Tex.) were imaged using protocols which were approved by the Baylor College of Medicine Institutional Animal Care and Use Committee. The animals were anesthetized, intubated, and maintained with isoflurane. Animal body temperature was maintained at 100° F. using a warming blanket. At the end of the procedure, the animals were euthanized and lymph nodes resected with fluorescence guidance. Swine were chosen for the lymph mapping study because swine dermis and lymphatic plexus of swine is considered most comparable to humans.

NIR Fluorescence Enhanced Imaging

Continuous-wave optical imaging of the fluorescent NIR dyes was performed with a custom built intensified charged-coupled device (CCD). Reynolds J S, Troy T L, and Sevick-Muraca E M. *Multipixel techniques for frequency-domain photon migration imaging*. Biotechnol Prog 13: 669-680, 1997, incorporated herein by reference in its entirety for all purposes. Briefly, the device had three principal components: 1) a NIR-sensitive image intensifier (model FS9910C ITT Night Vision, Roanoke, Va.); 2) a 16-bit dynamic range, frame transfer CCD camera (Roper Scientific, Tucson, Ariz.); and 3) a 785-nm laser diode (Thorlabs) used to provide the excitation light for activating ICG and hyaluronan-NIR. The 785-nm laser diode beam was expanded by using a planoconvex lens and a holographic optical diffuser such that approximately 0.08 $m^2$ of the swine's body was illuminated. A 785-nm holographic notch band rejection filter (model HNPF-785.0-2.0, Kaiser Optical Systems, Ann Arbor, Mich.) and an 830-nm image quality bandpass filter (model 830.0-2.0, Andover, Salem, N.H.) were placed before the 28-mm Nikkor lens (Nikon) to selectively reject the excitation light and pass the emitted 830-nm wavelength. A total of 400 to 1,000 images with 512×512 resolution and 200 ms exposure time were acquired enabling near-real time visualization of ICG trafficking. For image registration, white light images were acquired by replacing the holographic and bandpass filters with a neutral density filter and illuminating the surface of the swine with a low-power lamp.

Image Analysis

Images were processed using MATLAB (The Mathworks, Natick, Mass.), ImageJ (National Institutes of Health, Bethesda, Md.), and V++ (Digital Optics, Auckland, New Zealand). ImageJ is an image analysis and processing program and supports optical imaging file formats. V++ is the Roper Scientific CCD camera software interface with programmable modules for ICCD operation. MATLAB was used to compute average velocity and frequency of pulsatile lymph flow. To reveal the frequency of the pulsatile flow, which is a characteristic of pumping lymphatics, the mean fluorescence intensity from a fixed region of interest on a lymph channel was selected and plotted as a function of imaging time. Average velocity was computed by tracking the position of a "bolus" of ICG pulse moving along the length of a lymph channel.

Results

Real Time Imaging of Lymph Function

Figure 7:
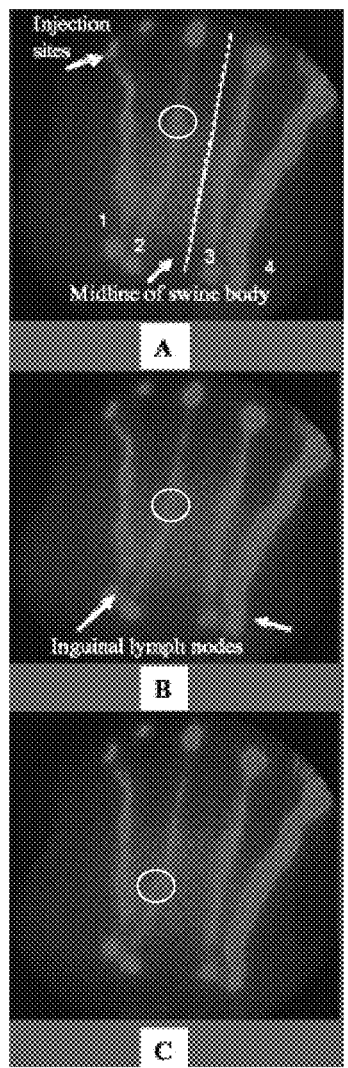
FIGS. 7A-C show organic dye trafficking in abdominal lymph vessel of swine: A) organic dye packet (circle) collected in a vessel segment; B) Organic dye packet pushed forward to next vessel segment; C) Still from a movie at 60 seconds after image taken in (A)

FIG. 7 represents a typical set of image frames from a movie depicting nonspecific ICG trafficking in the lymph vessels of the swine abdomen after four 200-µL injections of 32 µM ICG using the "research catheter set" at the level of the third teats. Each imaged lymph vessel was associated with a single injection site. Lymph propulsion was visualized immediately upon administration of ICG. The vessels 1 and 4 in FIG. 2 drain to the superficial mammary nodes (also known as the inguinal nodes), and the vessels 2 and 3 drain to the subiliac lymph nodes that are located 2.5- to 3-cm deep. The H&E and NIR fluorescence micrographs of resected fluorescent tissues confirmed dye deposition within the lymph nodes. The still frames were taken at intervals of 36 and 60 seconds, and the circle in FIG. 7 depicts a typical "packet" of ICG transiting the 12-cm long lymph vessel. Whereas ICG propulsion is not directly evident in all the lymph vessels in the still frames, quantitative analysis of the movie demonstrates that similar trafficking was seen in the three other lymph vessels.

Figure 8:
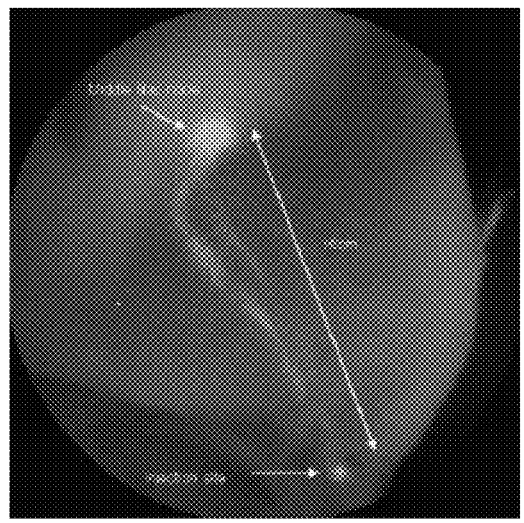
FIG. 8 is a snapshot of organic dye being propelled from the hindlimb to the middle iliac lymph node in swine.

FIG. 8 presents an overlay of white light image of the swine's anterior hindlimb and a typical fluorescent image frame from a movie depicting ICG trafficking in leg lymph vessel. Upon intradermal delivery of 200 µl of 32 µM ICG using a "microcone" device, lymph flow immediately progressed from the site of injection to the middle iliac node and continued for 4 hours, the duration for which the animal was anesthetized. The middle iliac node was already fluorescent before the intradermal injection in the hindlimb due to ICG drainage from the subiliac nodes from previous abdominal imaging as shown in FIG. 2. The movie also demonstrated propulsive lymph flow in the hindlimb as seen in the abdominal area.

Analysis of Lymph Function

Figure 9A:
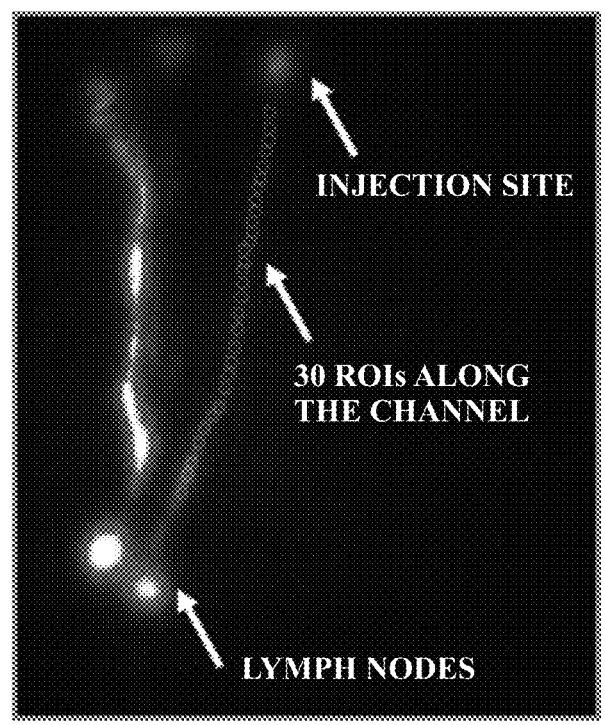
FIG. 9A shows the position of ROIs selected along the length of a channel to track averaged intensity change at each region selected along the length of the channel for the complete duration of imaging.
Figure 9B:
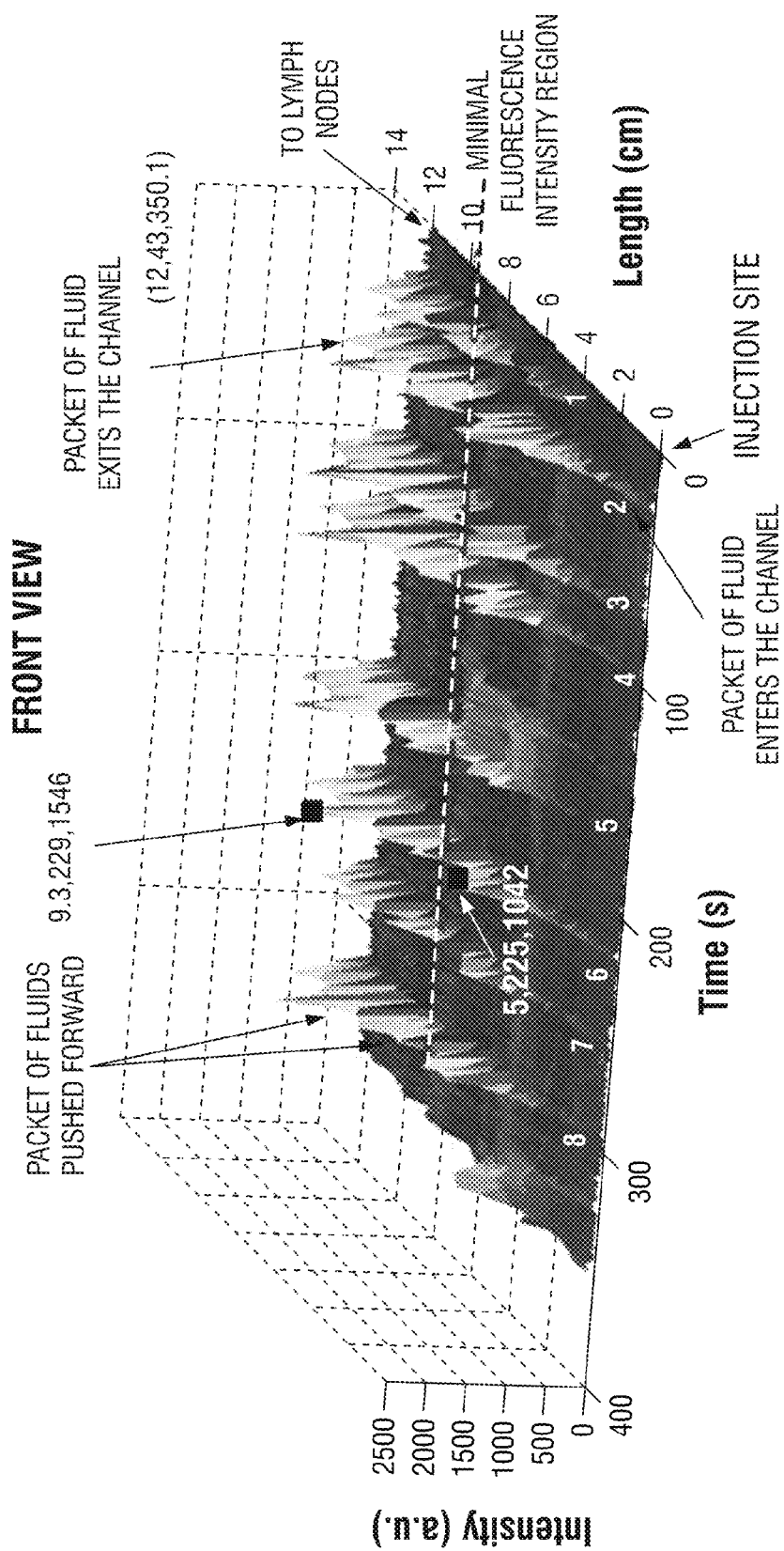
FIGS. 9B-9C are three dimensional plots of intensity profile of organic dye as a function of vessel length and time: (B) Front view of a three-dimensional plot of intensity profile at selected ROIs as a function of length of vessel and time of imaging; (C) Top view of the same 3D plot that depicts trails of trafficking dye along the channel length in real time.
Figure 9C:
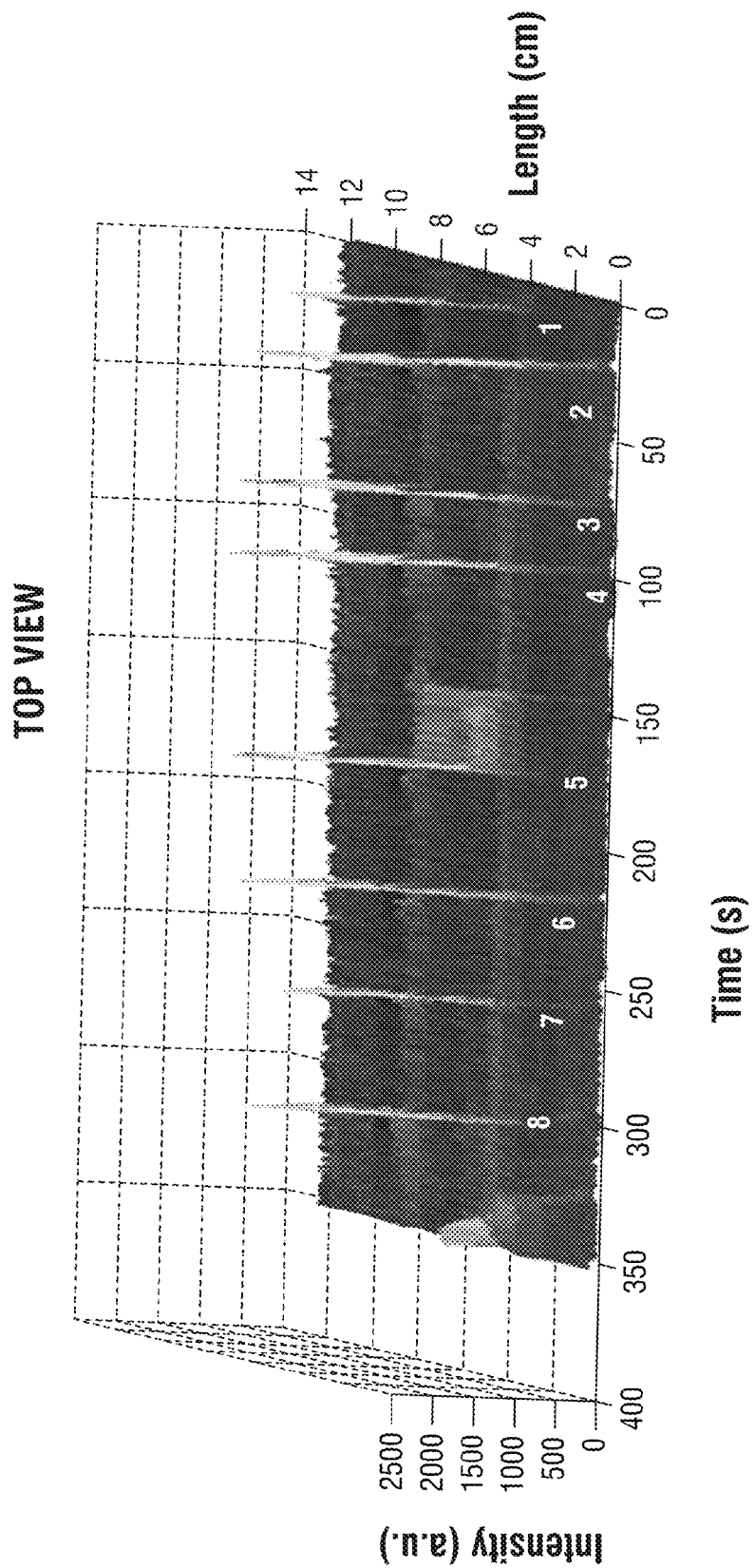

To quantify pulsatile lymph flow, a stationary, circular region of interest (ROI) was identified on a fluorescent lymph vessel as shown in FIG. 3A. FIG. 3B depicts the fluorescent intensity counts within the ROI as a function of time over 7 minutes of imaging time. The fluorescence intensity profile illustrates the typical, spontaneous propulsive lymph flow as indicated by the fluorescence intensity peaks repeating on an average of every 46 seconds when an ICG "packet" was propelled from the injection site toward the lymph node in the second (from left) abdominal afferent lymph vessel. As depicted in FIG. 9A, ROIs were identified across the length of the vessel. FIGS. 9B and 9C illustrate different views of a three-dimensional plot of fluorescence intensity as a function of vessel length and elapsed time after intradermal injection of 200 µl of 32 µM ICG within the second abdominal lymph vessel. The plot depicts eight trails of ICG packets (enumerated in FIGS. 9B and 9C) that were propelled from the injection site (at length of about 0 cm) to the lymph node (at length of about 12.5 cm). For example, at time 225 seconds, an ICG packet was present at 5 cm from the injection site. Lymphangion contractions propelled the ICG forward, and after 4 additional seconds, the bolus was at 9.3 cm from the injection site. There was only one ICG packet present at any one time in one segment of the lymph vessel. As can be seen in FIG. 9B, each packet consistently accumulated within a certain segment of the lymph vessel before being emptied into a downstream section of the vessel. FIG. 9C depicts the top view of FIG. 9B. FIG. 9C (shown only for added clarity) illustrates eight ICG packets transiting along the lymph channels as a function of time.

The functional status of lymph channels was also characterized by measuring velocity of transiting ICG "packets." FIG. 4 is a plot of ROI fluorescent intensity as a function of vessel length from the site of administration at 28 seconds, 30 seconds, and 35 seconds. Superimposed on each plot are the time-averaged ROI fluorescent intensities with standard deviations plotted as a function of vessel length.

The values of lymph flow velocities and pulse frequencies were computed from imaging on six abdomens and three hindlimb regional lymph vessels. Upon intradermal injection of ICG in the swine's leg, the leg lymph vessel was observed to immediately take up the dye and propel the ICG "packets" toward the middle iliac lymph node at a frequency ranging from 3.3 to 6.2 pulses of ICG per minute and at a velocity ranging from 0.33 to 0.46 cm/s. Four hours after an injection on the leg, the lymph vessel still depicted active lymphangion contraction by propelling ICG "packets" at a rate of 1.3 pulses/min and at a velocity of 0.62±0.23 cm/s. We also observed a range of velocities from 0.23 to 0.75 cm/s for ICG "packets" transiting in the abdominal lymph vessels, and each bolus of ICG dye or pulse of ICG passed through a fixed location on the vessel at a frequency of 0.5-1.3 pulses/min following 200 µl injection of 32 µM ICG. The rate of propulsion did not correlate to respiration or heart rate.

Dynamic Imaging of Lymph Propulsion in Humans

The above disclosed method of imaging lymphatic function was successfully performed on normal human subjects. The instrumentation required for normal human subjects consisted of a frame transfer CCD camera, a near-infrared sensitive image intensifier, optics for efficiently collecting and filtering the emitted fluorescence, and incident excitation light from a laser diode illuminating the tissues with less than 1.9 mW/cm2 of tissue. Imaging of lymph function was performed on the arms and legs of human subjects.

Figure 12:
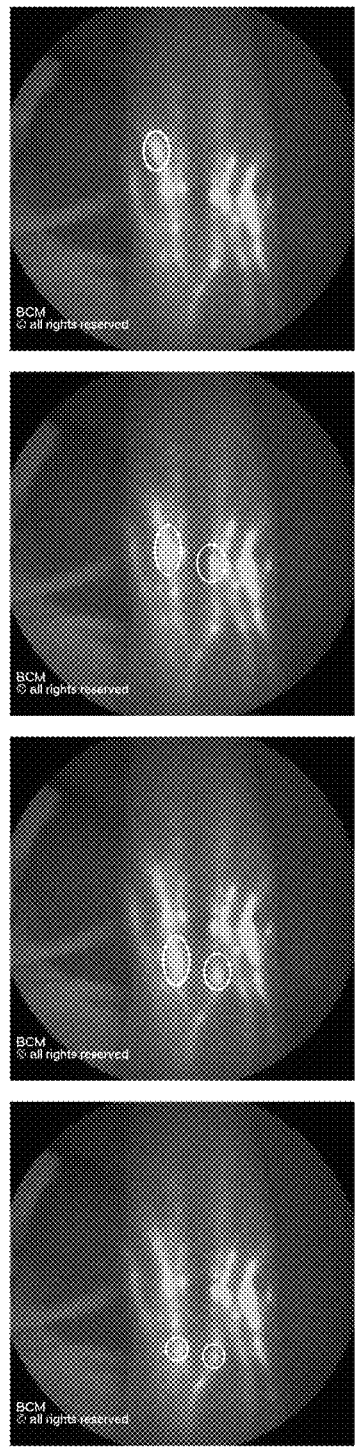
FIG. 12 shows images of lymph propulsion in a human subject.

FIG. 12 contains a series of white light photographs of the ventral (inner) arm with the elbow in the center of the image and fluorescent overlays of lymph flow at times of 0, 1.8, 4.21, 5.46 seconds (from top to bottom). Four interdigit, intradermal injections of 25 micrograms of ICG resulted in lymph propulsion through several lymphatic vessels (denoted by the green overlay). Lymph flow occurred from the interdigit injection sites (located at the top but out of the field of view), to the cubital lymph nodes within the elbow, towards the upper arm and axillary lymph nodes. The white circles denote packets of ICG flowing through the lymphatic system. Measurement of velocity of these packets may provide a quantitative measure of lymph sufficiency in humans.

EXAMPLE 2

Modification of IR-783 Dye

IR-783 was combined with 4 mercaptobenzoic acid in presence of ethyldiisopropylamine (DIPEA). The mixture was stirred for eight hours under nitrogen atmosphere and dimethyl formic acid solvent was removed. The compound 1 (IR-783-S-Ph-COOH) was purified by flash chromatography.

Compound 1 was treated with hydroxysuccinamide (HOSu) in dimethylformamide (DMF) and purified to obtain compound 2 (IR-783-S-Ph-COOSu). Compound 2 was combined with mono-Trityl 1,6-diaminohexan acetic acid salt in DMF and DIPEA. The mixture was stirred overnight to remove solvent and the residue (compound 3) was dissolved in methanol and purified by flash chromatography. Finally, compound 3 was mixed with 40% TFA (trifluoro acetic acid) in DCM (dichloromethane). The mixture was stirred for 30 minutes to remove the solvent. The residue was washed with ether several times and purified by HPLC (high pressure liquid chromatography).

Conjugation of Modified IR-783 to HA

Modified IR-783, hyaluronan, N-Hydroxybenzotriazole (HOBt) and benzotriazol-1-yl-oxytripyrrolidinophosphonium hexafluorophosphate (PyBop) were combined in dimethylformamide (DMF). DIPEA was added to this mixture. The mixture was stirred for four hours. After solvent removal residue was washed with ether and ethyl acetate several times. The final compound was subjected to TLC, thin layer chromatography to identify the purified compound.

Staining of Lymph Vessels with HA-NIR Molecule

Figure 10:
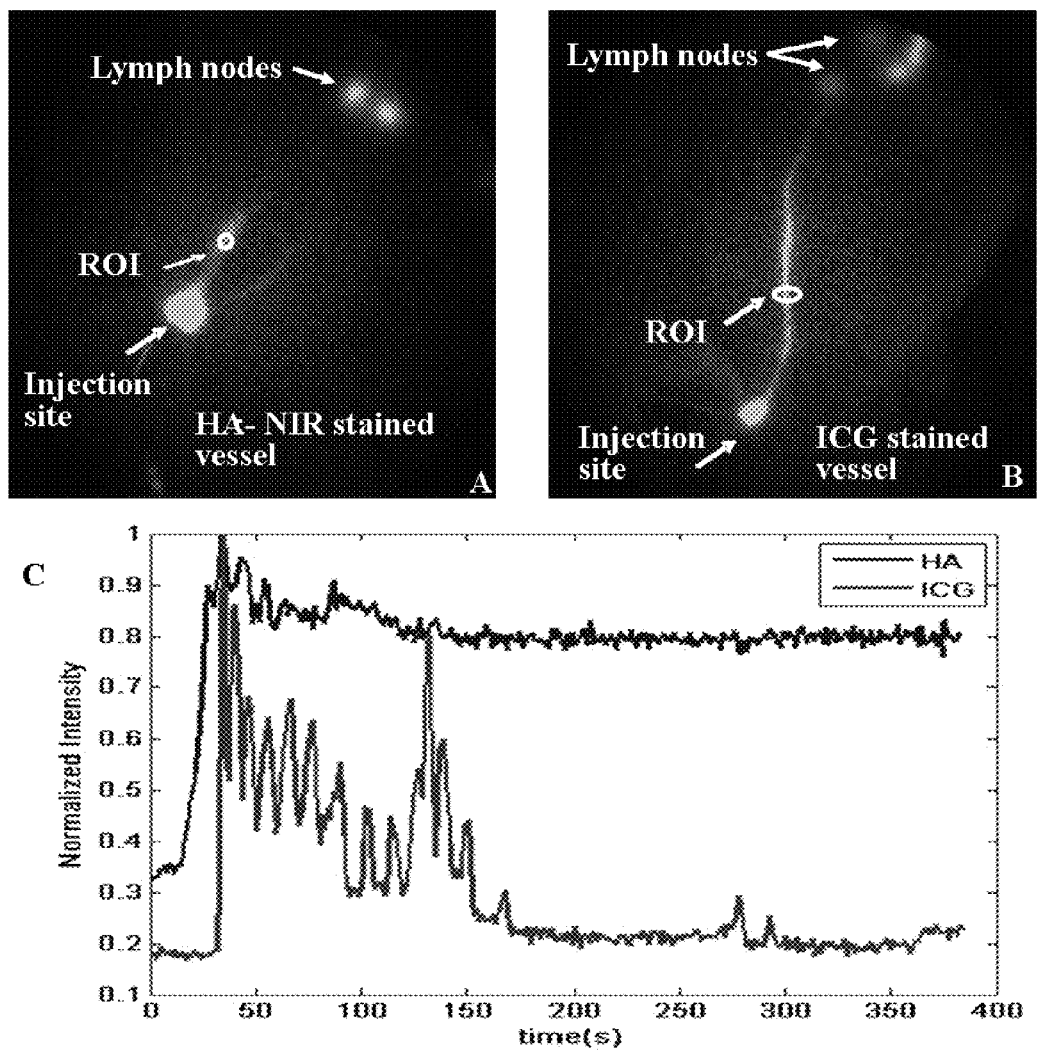
FIGS. 10A-10C show a mean fluorescent intensity plot of leg lymph vessel stained with HA-NIR and indocyanine green (ICG) at a fixed ROI for dynamic imaging time.

FIGS. 10A and 10B, represent fluorescent images arising from intradermal injection of 150 µl of 64 µM hyaluronan conjugate (HA-NIR) and 32 µM ICG in the swine hindlimb vessel. Unlike the free, nonspecific ICG dye, HA-NIR "stained" the lymph vessel walls as it filled the vessel. Propulsion of packets of HA-NIR was not observed as was observed for ICG.

Instead, HA-NIR uniformly demarcated the lymphatic vessels and lymph nodes for as long as the imaging study was conducted (4 h). With the use of the ROIs indicated on FIGS. 10A and 10B, the normalized fluorescent intensity values were plotted for the lymph vessels imaged with HA-NIR and ICG. Whereas fluctuation and net reduction of intensity as a function of time was seen for fluorescence owing to ICG lymph trafficking, FIG. 10C shows that the fluorescence intensity due to HA-NIR was almost constant and remained unchanged for the duration of image acquisition 6 min. The observation was consistent with the binding of HA-NIR to LYVE-1 present on the lymph endothelium.

Figure 11A:
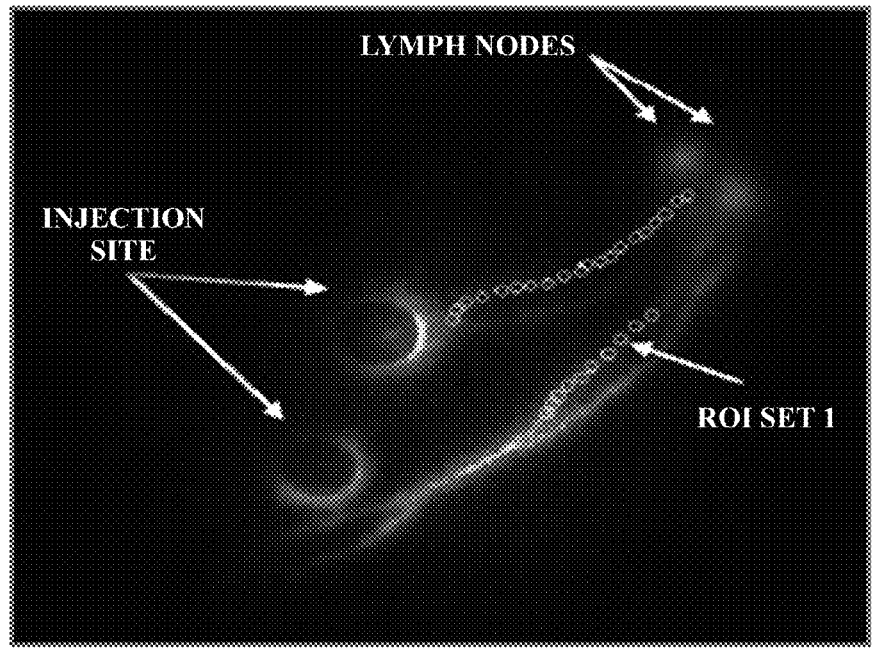
FIGS. 11A-B are fluorescent image of swine's leg lymph vessel stained with an embodiment of a modified imaging agent (HA-NIR)
Figure 11B:
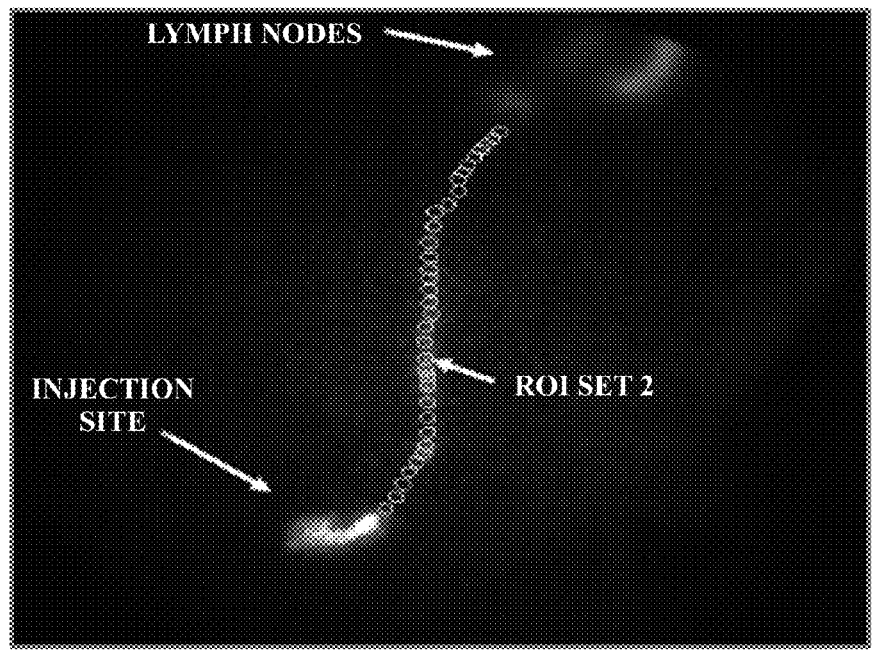
Figure 11C:
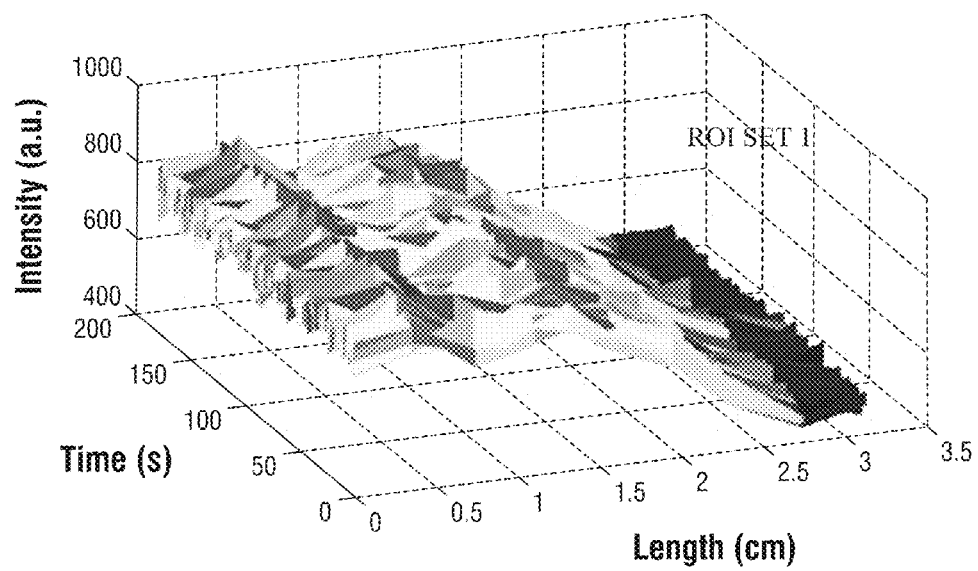
FIG. 11C is a three dimensional plot of intensity (arbitrary units (a.u.)) vs time(s) vs length (cm) of the vessel that shows change in intensity along the length of a channel during dynamic imaging of modified imaging agent staining the vessel wall.
Figure 11D:
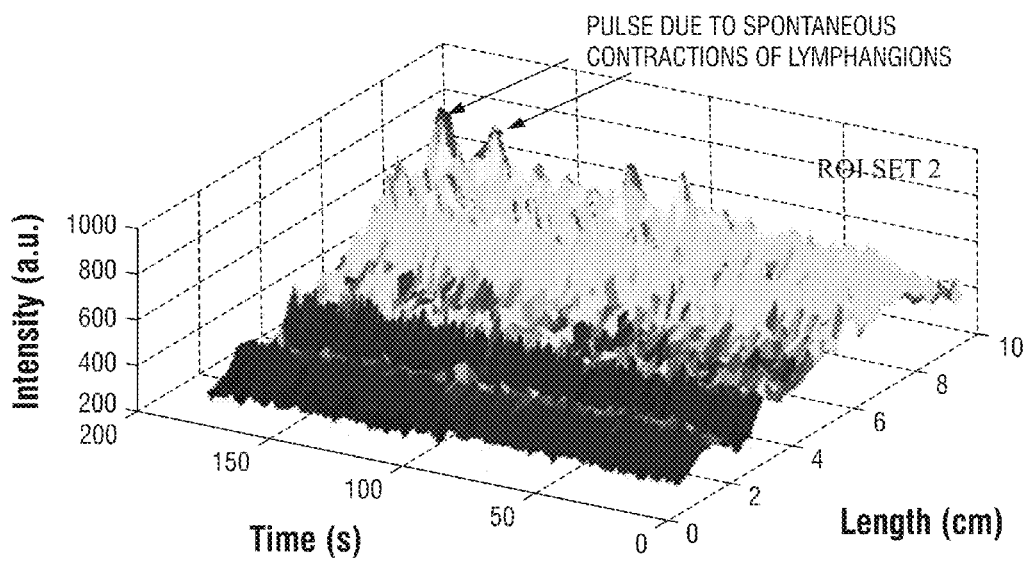
FIG. 11D is a three dimensional plot for unmodified organic dye flowing in the leg lymph vessel.

To better display the differences between HA-NIR and ICG, FIGS. 11C and 11D show the three-dimensional plots of fluorescent intensity as a function of vessel length and time for HA-NIR dye and the nonspecific ICG in swine lymph vessels. For HA-NIR, the intensity remained constant with time but diminished along the length of the vessel at increasing distances away from the injection site. This observation may be explained by either the variation in the depth of the vessel as it drained into the lymph node or due to the binding of HA-NIR to LYVE-1 and subsequent depletion of unbound HA-NIR as it transited along the lymph vessel away from the site of injection. On the other hand, the fluorescence intensity due to ICG varies with time and length along the vessel, showed "spikes" associated perhaps with the spontaneous lymphangion contractions and a reduction of intensity owing to its exit from the lymph channel.

Use of HA-Modified Imaging Agent as a Report of Hyaluronidase Activity

Figure 13:
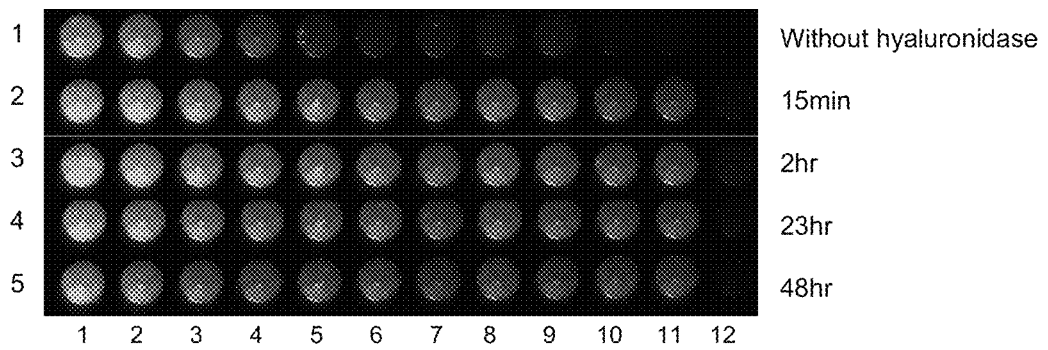
FIG. 13 shows different concentrations of modified imaging agent (HA-modified IR-783) incubated with different concentration of hyaluronidase.

FIG. 13 shows different concentrations of conjugated imaging agents incubated with different concentrations of hyaluronidase. The vertical lanes consist of unmodified imaging agent alone (lane 1) and increasing concentration of conjugated imaging agents (lanes 1-12). Without hyaluronidase present (top row), increased fluorescence quenching occurred with increased dye loading. In the presence of 12.5 units of hyaluronidase, conjugates in lanes 5 through 11 had reduced quenching and increased fluorescent yield. The table below shows the different imaging agent concentration in each lane.

TABLE 1

Concentrations of modified imaging agent in lanes 1-12 for FIG. 13

| 1: dye | 2: HA-dye 1% | 3: HA-dye 2% | 4: HA-dye 4% |
|---|---|---|---|
| 5: HA-dye 5% | 6: HA-dye 6% | 7: HA-dye 7% | 8: HA-dye 8% |
| 9: HA-dye 9% | 10: HA-dye 12% | 11: HA-dye 17% | 12: HA-dye 100% |

When the molar percentage of modified IRDye783 was decreased (in lanes shown in FIG. 13), the fluorescent yield was reduced, suggesting the close spacing of the dye molecules may have caused quenching (as seen in the top horizontal row in FIG. 13). However, when hyaluronidase, the natural enzyme of HA was added (rows 2-5), the cleavage of the HA polysaccharide may have resulted in a reduction in the quenching and an increase in fluorescent yield.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference in the Description of the Related Art is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A method of measuring lymph propulsion within lymphangions and lymph vessels comprising:
    a) administering a non-particulate fluorescent organic dye to a tissue that is drained by a lymph structure, wherein the dye is picked up and transited by lymph fluid through the lymph;
    b) illuminating the tissue surface adjacent to the lymph vessel with excitation light to excite the organic dye carried by the lymph fluid within lymphangions comprising the lymph vessels;
    c) repeatedly imaging the fluorescent light emitted by the organic dye for acquisition times of about 10 milliseconds to about 1 second, producing a series of single images, wherein said series of single images are collected over a period of about 1 second to about 30 minutes; and
    d) analyzing the images, wherein said analyzing comprises:
        (a) calculating a velocity for packets of dye carried by said lymph fluid pumped to sequential lymphangions;
        (b) calculating a propulsion frequency for the packets of dye pumped to individual lymphangions, and determining the rate of flow and frequency of propulsion of lymph fluid through the lymph structure.

2. The method of claim 1 wherein (a) comprises injecting the organic fluorescent dye subcutaneously to the one or more lymph structures.

3. The method of claim 1 wherein (a) comprises using a catheter to inject the organic dye intradermally into the one or more lymph structures.

4. The method of claim 1 wherein the organic dye comprises tricarbocyanine dyes, bis(carbocyanine) dyes, dicarbocyanine dyes, indol-containing dyes, polymethine dyes, acridines, anthraquinones, benzimidazols, indolenines, napthalimides, oxazines, oxonols, polyenes, porphins, squaraines, styryls, thiazols, xanthins, or combinations thereof.

5. The method of claim 1 wherein the organic dye is indocyanine green (ICG).

6. The method of claim 1 wherein the organic dye has an excitation wavelength ranging from about 750 nm to about 900 nm.

7. The method of claim 1 wherein the excitation light has a wavelength ranging from about 700 nm to about 800 nm.

8. The method of claim 1, wherein (c) comprises using an intensified charge-coupled camera.

9. The method of claim 1 wherein the lymphatic structures is at least about 3 cm beneath the tissue surface.

10. The method of claim 1 wherein (b) comprises illuminating the tissue surface with an excitation light source selected from group consisting of laser diodes, semiconductor laser diodes, gas lasers, light emitting diodes, and combinations thereof.

11. The method of claim 1 wherein (c) comprises measuring a peak in fluorescent intensity at a target region to determine frequency of propulsion of the lymph vessels.

12. The method of claim 1 wherein (c) comprises defining a plurality of target regions and measuring a change in fluorescent intensity at each target region to determine the lymph flow velocity within each lymphatic vessel.

13. The method of claim 1 wherein (c) comprises using tomographic imaging techniques to capture three-dimensional images of lymph fluid propulsion.

14. A method of determining frequency of propulsion within lymphangions and lymph vessels comprising:
    a) administering a non-particulate fluorescent organic dye to a tissue that is drained by a lymph structure, wherein the dye is associated with lymph fluid and carried by the lymph fluid through the lymph structure;
    b) illuminating the tissue surface adjacent to the lymph vessel with excitation light to excite the organic dye carried by the lymph fluid within lymphangions comprising the lymph vessels;
    c) determining a target region of the lymphangions comprising the lymph vessels;
    d) repeatedly measuring fluorescent intensity from the organic dye at the target region for a time period of at least 1 min; and
    e) determining a number of fluorescent intensity peaks over the time period, the intensity peaks representing one or more packets of organic dye being propelled through, and dividing the number of intensity peaks by the time period to determine the frequency of propulsion of the lymphangions.

15. A method of determining lymph fluid flow velocity within lymphangions and lymph vessels comprising:
    a) administering a non-particulate fluorescent organic dye to a tissue that is drained by a lymph structure, wherein the dye is associated with lymph fluid and carried by the lymph fluid through the lymph structure;
    b) illuminating the tissue surface adjacent to the lymphatic vessel with excitation light to excite the organic dye carried by the lymph fluid within lymphangions comprising the lymph vessels;
    c) determining at least a first and a second target region along the lymphangions comprising lymph vessels having a distance between the first and second target regions;
    d) measuring a time period for a packet of organic dye to pass through the target regions;
    e) dividing the distance by the time period to determine the lymph fluid flow velocity in the lymphangions and lymph vessels.

16. The method of claim 15 wherein (d) comprises measuring the time period elapsed between detecting a fluorescent intensity peak at each target region.

17. The method of claim 15 wherein the distance comprises the entire length of a lymph structures.

* * * * *